(12) United States Patent
Gill

(10) Patent No.: US 12,070,570 B2
(45) Date of Patent: Aug. 27, 2024

(54) INJECTABLES

(71) Applicant: Safe IV Ltd., Manchester (GB)

(72) Inventor: Steven Gill, Leeds (GB)

(73) Assignee: Safe IV Ltd., Manchester (GB)

( * ) Notice: Subject to any disclaimer, the term of this patent is extended or adjusted under 35 U.S.C. 154(b) by 31 days.

(21) Appl. No.: 15/569,553

(22) PCT Filed: Apr. 29, 2016

(86) PCT No.: PCT/GB2016/051251
§ 371 (c)(1),
(2) Date: Oct. 26, 2017

(87) PCT Pub. No.: WO2016/174471
PCT Pub. Date: Nov. 3, 2016

(65) Prior Publication Data
US 2018/0250467 A1    Sep. 6, 2018

(30) Foreign Application Priority Data

Apr. 30, 2015 (GB) .................................. 1507395

(51) Int. Cl.
| | | |
|---|---|---|
| *A61M 5/14* | (2006.01) | |
| *A61M 5/00* | (2006.01) | |
| *A61M 5/168* | (2006.01) | |
| *A61M 39/16* | (2006.01) | |
| *A61M 25/00* | (2006.01) | |

(52) U.S. Cl.
CPC .............. *A61M 5/14* (2013.01); *A61M 5/007* (2013.01); *A61M 5/16831* (2013.01); *A61M 39/16* (2013.01); *A61M 2005/1403* (2013.01); *A61M 2025/0019* (2013.01); *A61M 2205/583* (2013.01); *A61M 2205/584* (2013.01)

(58) Field of Classification Search
CPC .......... A61M 5/007; A61M 2005/1403; A61M 2005/1787; A61M 2025/0019; A61M 2039/0018; A61M 2205/583; A61M 2205/584
See application file for complete search history.

(56) References Cited

U.S. PATENT DOCUMENTS

| | | | | | |
|---|---|---|---|---|---|
| 4,935,009 | A | * | 6/1990 | Caldwell | A61M 5/1424 604/218 |
| 5,060,825 | A | * | 10/1991 | Palmer | A61C 1/0084 222/25 |
| 5,183,463 | A | * | 2/1993 | Debbas | A61B 17/3403 604/915 |
| 5,417,667 | A | * | 5/1995 | Tennican | F16K 11/0655 604/248 |
| 2003/0007891 | A1 | * | 1/2003 | Wilson | G01M 3/222 422/400 |
| 2003/0118567 | A1 | * | 6/2003 | Stewart | C12N 5/0691 435/366 |
| 2007/0207996 | A1 | * | 9/2007 | Auger | A61K 31/282 514/210.21 |
| 2009/0156562 | A1 | * | 6/2009 | Winch | A61K 9/0019 514/130 |
| 2009/0327204 | A1 | * | 12/2009 | Gilhuly | G06F 19/00 706/54 |
| 2010/0062981 | A1 | * | 3/2010 | Jeppsson | A61K 38/363 514/1.1 |
| 2010/0145274 | A1 | | 6/2010 | Royce | |
| 2010/0292672 | A1 | * | 11/2010 | Lee | A61M 5/31596 604/518 |
| 2013/0079746 | A1 | * | 3/2013 | Fischell | A61M 25/01 604/506 |
| 2014/0271897 | A1 | * | 9/2014 | Pathak | A61K 9/5031 424/497 |
| 2014/0350486 | A1 | * | 11/2014 | Cordes | A61M 5/14 604/258 |

FOREIGN PATENT DOCUMENTS

| | | | |
|---|---|---|---|
| DE | 102004050669 A1 | 4/2006 | |
| RU | 2009113712 A | 10/2010 | |
| WO | 1997044074 A1 | 11/1997 | |
| WO | WO-2006027361 A2 * | 3/2006 | ............. A61L 29/14 |
| WO | 2008011581 A2 | 1/2008 | |
| WO | 2013066742 A1 | 5/2013 | |

OTHER PUBLICATIONS

Notification of Transmittal of the International Search Report and the Written Opinion of the International Searching Authority, or the Declarations; PCT/GB2016/051251; Apr. 29, 2016.
Written Opinion of the International Searching Authority; PCT/GB2016/051251; Apr. 29, 2016.
Intellectual Property Office, Search Report, Application GB1507395.0, Oct. 30, 2015.
Pearson, Ashley, Going bananas for IV: The A-lister's new diet craze involving an intravenous drip and a bag full of vitamins, Daily Mail, 2012, online: https://www.dailymail.co.uk/femail/article-1055814/Going-bananas-IV-The-A-listers-new-diet-craze-involving-intravenous-drip-bag-vitamins.html.

\* cited by examiner

*Primary Examiner* — Kami A Bosworth
(74) *Attorney, Agent, or Firm* — E. Eric Mills; Nicholas P. Stadnyk; Maynard Nexsen PC

(57) ABSTRACT

The present invention relates to methods and products for demonstrating that intravenous access devices are substantially or completely void of residual drug products. The methods and products involve the use of colored liquids to allow the visual assessment of whether or not an intravenous device has been flushed.

14 Claims, No Drawings

INJECTABLES

The present invention relates to methods and products for demonstrating that intravenous access devices are substantially or completely void of residual drug products.

BACKGROUND

Since January 2011 there have been 16 reported incidences in the UK of unexpected cardiac or respiratory arrest due to the flushing of residual anaesthetic drugs left in the dead space of intravenous cannulae. These are the ones that have been reported to the National Reporting and Learning System and there will undoubtedly be more that have not been detected or recognised. Of these at least 7 resulted in moderate or severe harm to the patient.

After intravenous anaesthesia, a small amount of drug is typically left in the dead space of the cannula and if the cannula is not flushed this can result in the residual drug being administered to the patient the next time the cannula is used to administer fluids or medications. This inadvertent administration often occurs sometime after the patient has left theatre and when they are in a less intensively monitored environment such as in a general ward. The quantity of drug administered in this way is typically small but it can be enough to cause respiratory arrest particularly in the paediatric population where the resultant dose is larger relative to body weight. Nevertheless, at least 8 of the recorded incidents have occurred in patients over 16 years of age.

There is a trend currently towards the use of long term access devices that contain a larger dead space. There is also an increased use of portless cannulae that have extensions that increase the amount of dead space. These devices are used because they allow a more effective decontamination of the injection port prior to drug administration in an effort to reduce hospital acquired infections. The increased use of cannulae having a larger dead space is thus the result of increasing adoption of such cannulae as clinical best practice. It is expected that the increased use of such cannulae will lead to larger doses of drugs being inadvertently delivered to patients in the manner described above. Thus, the increased use of such cannulae in the clinical environment is likely to lead to an increase in the number of incidents in which residual drugs are inadvertently administered to patients and/or the severity of these incidents in the future.

There is currently a national campaign in the UK to increase awareness of this problem with an emphasis on encouraging the flushing of intravenous access devices prior to patients leaving the theatre environment. One problem with this flushing is that the solution that is commonly used to flush the access device (0.9% NaCl) is a transparent colourless fluid which is indistinguishable from the group of drugs that mostly cause these problems (i.e. muscle relaxants and other anaesthetics). There is a particular problem when a patient has more than one access device as it may be that one device is flushed but not the other(s).

Bowman et al (Residual anaesthesia drug in intravenous lines—a silent threat?; Anaesthesia, 2013, 68, 551-561) discusses the issue and proposes increased checks in the post-surgical patient transfer protocols as a solution to the problem and as a means for increasing awareness. Ogleby et al (Residual anaesthesia drug in intravenous lines—silent threat, visible solutions?; Anaesthesia, 2013, 68, 551-561) proposed, in addition to the improved patient transfer protocols suggested by Bowman et al, the use of eye-catching safety posters to further raise awareness.

BRIEF SUMMARY OF THE DISCLOSURE

In a first aspect of the invention there is provided a visual method of assessing if a residual drug product is resident or remains in an intravenous access device, the method comprising the step of:
    determining by sight whether a coloured liquid is resident in the intravenous access device.

In certain alternative aspects of the first aspect, the presence of a coloured liquid indicates that no or substantially no residual drug product is present in the intravenous access device. This will be the case where the drug product was administered as part of a colourless or differently coloured liquid and the intravenous access device has subsequently been flushed with a coloured liquid. The presence of a liquid having that colour in the intravenous access device would indicate that the device had been completely or substantially flushed.

In certain embodiments of the first aspect, the presence of a coloured liquid indicates that residual drug product may be present in the intravenous access device. This will be the case where the drug product was administered as a component of a coloured liquid and the device should subsequently have been flushed with a colourless liquid. The presence of a solution having that colour in the intravenous access device would indicate to the clinician or medical attendant that the device had not been completely or substantially flushed.

In a second aspect of the invention there is provided a method of flushing an intravenous access device, the method comprising:
    passing a pharmaceutically acceptable coloured liquid through the intravenous access device.

In a third aspect of the invention is provided a method of demonstrating that no or substantially no drug product is resident or remains in an intravenous access device, the method comprising:
    passing a pharmaceutically acceptable coloured liquid through the intravenous access device.

In a fourth aspect of the invention is provided a method of administering intravenously a drug product to a subject in need thereof, the method comprising:
    administering the drug product to the subject via an intravenous access device; and
    passing a pharmaceutically acceptable coloured liquid through the intravenous access device.

It may be that a colourless flush solution is passed through the intravenous access device prior to the pharmaceutically acceptable coloured liquid. The colourless flush solution will be pharmaceutically acceptable and will not contain any drug product. The flush solution may be a saline solution. This may be the case if, for example, there is any concern regarding the compatibility of the drug product and the coloured compounds in the coloured solution.

In a fifth aspect of the invention is provided a pharmaceutically acceptable coloured liquid for use in flushing an intravenous access device.

In a sixth aspect of the invention is provided the use of a pharmaceutically acceptable coloured liquid for flushing an intravenous access device.

In a seventh aspect of the invention is provided a kit for administering intravenously a drug product, the kit comprising:

a substantially colourless drug product in a form suitable for intravenous administration; and a pharmaceutically acceptable coloured liquid.

The coloured liquid will be different to the drug product.

The kit may also comprise a colourless flush solution, e.g. saline.

In an eighth aspect of the invention is provided a pharmaceutically acceptable coloured liquid for use in a method of treating a patient by administering a pharmaceutical product via an intravenous access device and then flushing the intravenous access device with the coloured liquid.

Thus, the invention may provide a coloured compound for use in a method of treating a patient by administering a pharmaceutical product via an intravenous access device and then flushing the intravenous access device with the coloured compound, the coloured compound being comprised in a pharmaceutically acceptable liquid.

In the second to eighth aspects of the invention, the coloured liquid is passed through the intravenous access device after a drug product has been administered. In certain specific examples, this will be done by an anaesthetist in theatre but it could be done by any medical professional who inserts or uses intravenous access devices. The vast majority of drug products for intravenous administration are substantially colourless. The presence of the coloured liquid in the device will then serve as a positive visual indication that any particular access device does not contain potentially harmful drugs and can therefore be used with confidence by medical professionals elsewhere, e.g. once the patient is on a general ward. It may be that the intravenous device is flushed with a colourless flush prior to the use of the coloured solution. This may be the case if, for example, there is any concern regarding the incompatibility of the drug product and the coloured compounds in the coloured solution.

In an ninth aspect of the invention is provided a pharmaceutically acceptable coloured liquid for intravenous administration, the liquid comprising a drug product.

In a tenth aspect of the invention is provided a kit for administering intravenously a drug product, the kit comprising:
the drug product in a pharmaceutically acceptable coloured liquid; and
a second pharmaceutically acceptable liquid, the second liquid being colourless or being a different colour to the first liquid.

In a eleventh aspect of the invention is provided a method of administering intravenously a drug product to a subject in need thereof, the method comprising the steps of:
administering the drug product in a pharmaceutically acceptable coloured liquid to the subject via an intravenous access device; and
passing a second pharmaceutically acceptable liquid through the intravenous access device, the second liquid being colourless or being a different colour to the first liquid.

In an twelfth aspect of the invention is provided a method of demonstrating that residual drug product is resident or remains in an intravenous access device, the method comprising:
passing a pharmaceutically acceptable coloured liquid comprising a drug product through the intravenous access device.

In the ninth to twelfth aspects of the invention, the drug product is provided as a coloured liquid. A colourless or different coloured second liquid is passed through the intravenous access device after the drug product has been administered. In certain specific examples, this will be done by an anaesthetist in theatre but it could be done by any medical professional who inserts or uses intravenous access devices. The presence of the colourless or differently coloured liquid in the device will then serve as a positive visual indication that any particular access device does not contain potentially harmful drugs and can therefore be used with confidence by medical professionals elsewhere, e.g. once the patient is on a general ward. Preferably, the second liquid is colourless.

In the second to eighth aspects of the invention, the coloured liquid preferably does not comprise a drug product. In the event that a compound that gives the coloured liquid its colour is itself a drug product (such as, for example, methylene blue), the coloured liquid preferably does not comprise any drug product other than the coloured compound. The coloured liquid may comprise an anticoagulant.

In the tenth and eleventh aspects of the invention the second liquid preferably does not comprise a drug product. The second liquid may comprise an anticoagulant.

The coloured liquid may be blue or green. Blue and green are colours particularly unlikely to be confused with blood or drug products. However, other colours, e.g. red, yellow, purple, orange or pink, could be used if so desired. This may be the case if, for example, compounds having those colours offer other beneficial properties, such as having no side effects or not interacting with other medications.

DETAILED DESCRIPTION

The term 'intravenous access device' includes any device which provides access to a patient's vasculature over a period of time (e.g. an hour or more) in order to enable repeated use. Illustrative examples include peripheral cannulae, central lines, multi-lumen central catheters, peripherally inserted central catheters (PICC line), long lines, Hickman lines, Broviac lines and ports. It also encompasses any tubing or extensions which are attached to the cannula or other device. The presence or absence of a coloured liquid can typically be seen more clearly in a tube or extension attached to a cannula than in the cannula itself.

A pharmaceutically acceptable liquid is one which is suitable for intravenous administration to humans. The liquid may be a solution, a suspension, an emulsion or a mixture thereof.

A pharmaceutically acceptable liquid will typically be water based. Illustrative aqueous base solutions include a saline solution (e.g. 0.9% or 0.45% saline), a dextrose solution (e.g. 5% dextrose in water or 5% dextrose in either 0.9% or 0.45% saline), Ringer's Solution, Lactated Ringer's Solution, Hartmann's solution.

A pharmaceutically acceptable liquid may be oil based.

A pharmaceutically acceptable liquid may be colloidal, e.g. albumin, plasma or gelofusine based.

Where the pharmaceutically acceptable liquid is coloured, it will contain one or more coloured compounds. Ideally, at the concentration at which the compound or compounds is present within the liquid, the compound or compounds have no pharmacological effects, be non-toxic, do not cause allergic reactions in a significant proportion of the population (e.g. greater than 95%, 99% or 99.9% of the population are not allergic to the compound or compounds), do not interact with other medications, and are safe in children. In practice, however, the compound or compounds could, at a concentration sufficient that a small amount of liquid has a readily discernible colour, have clinically acceptable toxicity levels and pharmacological side effects. The coloured compound or compounds may be selected from those on the US Food and Drug Administration database of approved excipients for drug products.

One illustrative example of a strongly coloured (blue) compound which is suitable for intravenous administration to humans is methylene blue (Methylthioninium chloride). Methylene blue has known side effects and is known to interact with other medications but these effects occur at concentrations much higher than that needed simply to colour a solution sufficiently blue to be readily recognisable. Thus, the coloured liquid may comprise methylene blue. Likewise, the coloured compound may be methylene blue.

Another illustrative example of a strongly coloured (green) compound which is suitable for intravenous administration to humans is Indocyanine Green.

Other dyes that could be used include Curcumin (E100); Riboflavin or Riboflavin-5'-phosphate (E101); Tartrazine (E102); Quinolone Yellow (E104); Sunset Yellow FCF (E110); Patent Blue V (E131); Indigo Carmine (E132); Brilliant Blue (E133); Chlorophylls and chlorophyllins (E140); Copper complexes of chlorophyll and chlorophyllins (E141); Green S (E142) and Fast Green FCF (E143).

Blue dyes which could be used in the coloured liquids of the invention include: Patent Blue V (E131) and Brilliant Blue (E133).

Green dyes which could be used in the coloured liquids of the invention include: Fast Green FCF (E143) and Green S (E142).

Green coloured liquids can also be formed by combining blue and yellow dyes. Examples of such combinations which could be used in the coloured liquids of the invention include: Patent Blue V (E131) and Quinolone Yellow (E104); or Brilliant Blue (E133) and Tartrazine (E102). It may be, however, that the coloured liquid includes a single coloured compound.

The coloured compound or compounds will be present in the coloured liquid at a concentration at which the colour can readily be seen. This concentration will vary depending on the compound and is readily determined by filling a piece of cannula tubing with sample solutions of the compound at a range of concentrations. For methylene blue, for example, a 0.1 mM solution in 0.9% saline provides a readily discernible blue colour in cannula tubing.

The concentration of the coloured compound in the liquid may thus be in the range 0.001 mM to 5 mM, e.g. from 0.05 mM to 1 mM or from 0.075 mM to 0.25 mM.

A pharmaceutically acceptable liquid may comprise additional additives. These may include stabilisers, viscosity modifiers, pH modifiers and/or surfactants.

Some coloured compounds are only coloured across a particular pH range, typically because the compound is only coloured in a particular state of protonation or deprotonation. For such compounds, the pH of the liquid will be such that the compound is in its coloured state.

The drug product may be selected from: muscle relaxants; anaesthetics, opioids and vasoactive substances such as inotropes and vasopressors. The drug product may be selected from: muscle relaxants; anaesthetics and opioids. In certain preferred embodiments, the drug product is a muscle relaxant.

Illustrative muscle relaxants include suxamethonium, atracurium, cis-atracurium, pancuronium, rocuronium and vecuronium.

Illustrative anaesthetics include etomidate, thiopentone, ketamine and midazolam.

Illustrative opioids include remifentanil, alfentanil, fentanyl, morphine, oxycodone, pethadine, tramadol, sufentanil and diamorphine.

Illustrative vasoactive substances include inotropes and vasopressors. Illustrative inotropes include adrenaline, dopamine, dobutamine and dopexamine. Illustrative vasopressors include noradrenaline, phenylephrine and metaraminol.

Illustrative anticoagulants include heparin.

The term 'substantially no drug product' is intended to mean that either no drug product in present or, if some drug product is present, a quantity of drug product which would not cause any adverse effect. The act of flushing an intravenous access device is unlikely to remove every molecule of a drug product from the device but it would be expected to leave only trace amounts of the drug product. 'Substantially no drug product' could mean that the drug product is present at a concentration lower than 5% (e.g. lower than 2% or lower than 1% or lower than 0.1%) of the concentration at which the drug product was originally administered.

The term 'flushing' means the act of passing a liquid through an intravenous access device in order to displace any liquid (e.g. a liquid containing residual drug product) which was resident in the dead space of the device.

The term 'passing through' means the act of applying a positive pressure to a liquid in order to push that liquid through the intravenous access device. This will typically be achieved using a syringe or syringe driver but a gravity driven drip could also be used. The amount of liquid passed through the device will typically be sufficient to leave substantially no drug product in the device. Passing through does not mean that all of the liquid is passed through the device. Sufficient liquid will be left in the device that the liquid is visible. It may be, for example, that a bolus of from 0.5 to 10 mL, e.g. a bolus of from 1 to 5 mL, is passed through the device.

The term 'residual' means the small portion of a larger volume of liquid (e.g. a drug product) which is left in the dead space within an intravenous access device once the larger volume of liquid has been administered to the patient via the device.

The term 'dead space' refers to the space inside the intravenous access device.

The term 'coloured' means that a liquid or compound reflects, transmits or emits light in the visible spectrum such that it appears to the observer to have a recognisable colour. It may be that the coloured liquid or compound fluoresces. It may be that the coloured compound is detectable under UV radiation but it is preferred that the liquid or compound reflects, transmits or emits light in the visible spectrum. The term 'coloured' is intended to exclude liquids that are milky and white or off-white (e.g. propofol emulsions).

The term 'substantially colourless' is intended to encompass liquids that are transparent or translucent and have no readily discernable pigmentation as well as those which are milky and white or off-white.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of administering intravenously a drug product to a human subject in need thereof, the method comprising:
   administering the drug product from a first syringe, a first syringe driver, or a first gravity driven drip to the human subject via an intravenous access device configured for repeated use with access to the human subject's vasculature over a period of time; and
   following the administration of the drug product and to enable further use of the intravenous access device, passing a pharmaceutically acceptable coloured liquid from a second syringe, a second syringe driver, or a second gravity driven drip through the intravenous access device, wherein a sufficient amount of the pharmaceutically acceptable coloured liquid remains in the intravenous access device to provide a positive visual indication to medical staff elsewhere to a location where the drug was administered that the pharmaceutically acceptable coloured liquid has passed through the intravenous access device and the drug product has been flushed from the intravenous access device and administered to the human subject; wherein the pharmaceutically acceptable coloured liquid does not comprise a drug product, and wherein the administered drug product is a muscle relaxant.

2. The method of claim 1, wherein a colourless flush solution is passed through the intravenous access device prior to the pharmaceutically acceptable coloured liquid.

3. The method of claim 1, wherein the pharmaceutically acceptable coloured liquid is green or blue.

4. The method of claim 1, wherein the muscle relaxant is selected from suxamethonium, atracurium, cis-atracurium, pancuronium, rocuronium and vecuronium.

5. The method of claim 1, wherein the pharmaceutically acceptable liquid comprises a coloured compound and the concentration of the coloured compound in the pharmaceutically acceptable coloured liquid is in the range 0.001 mM to 5 mM.

6. The method of claim 1, wherein the pharmaceutically acceptable coloured liquid comprises a coloured compound selected from Indocyanine Green, Curcumin (E100); Riboflavin or Riboflavin-5'-phosphate (E101); Tartrazine (E102); Quinolone Yellow (E104); Sunset Yellow FCF (E110); Patent Blue V (E131); Indigo Carmine (E132); Brilliant Blue (E133); Chlorophylls and chlorophyllins (E140); Copper complexes of chlorophyll and chlorophyllins (E141); Green S (E142) and Fast Green FCF (E143).

7. The method of claim 1, wherein the amount of the pharmaceutically acceptable coloured liquid is sufficient to displace substantially all of residual the drug product resident in a dead space of the intravenous access device.

8. The method of claim 1, wherein an amount of 0.5 mL to 10 mL of the pharmaceutically acceptable coloured liquid is passed through the intravenous access device.

9. The method of claim 1, wherein the drug product is administered with another pharmaceutically acceptable liquid, wherein the another pharmaceutically acceptable liquid is colourless or a different color than the pharmaceutically acceptable coloured liquid.

10. A method of administering intravenously a drug product to a human subject in need thereof, the method comprising:
    administering the drug product from a first syringe, a first syringe driver, or a first gravity driven drip to the human subject via an intravenous access device configured for repeated use with access to the human subject's vasculature over a period of time; and
    following the administration of the drug product and to enable further use of the intravenous access device, passing a pharmaceutically acceptable coloured liquid from a second syringe, a second syringe driver, a second or gravity driven drip through the intravenous access device, wherein a sufficient amount of the pharmaceutically acceptable coloured liquid remains in the intravenous access device to provide a positive visual indication to medical staff elsewhere to a location where the drug was administered that the pharmaceutically acceptable coloured liquid has passed through the intravenous access device and the drug product has been flushed from the intravenous access device and administered to the human subject; wherein the pharmaceutically acceptable coloured liquid comprises methylene blue and the pharmaceutically acceptable coloured liquid does not comprise any drug product other than methylene blue, and wherein the administered drug product is a muscle relaxant.

11. The method of claim 10, wherein a colourless flush solution is passed through the intravenous access device prior to the pharmaceutically acceptable coloured liquid.

12. The method of claim 10, wherein the pharmaceutically acceptable coloured liquid is blue.

13. The method of claim 10, wherein the muscle relaxant is selected from suxamethonium, atracurium, cis-atracurium, pancuronium, rocuronium and vecuronium.

14. The method of claim 10, wherein the concentration of the methylene blue in the pharmaceutically acceptable coloured liquid is in the range 0.001 mM to 5 mM.

* * * * *